(12) United States Patent
Tethrake et al.

(10) Patent No.: US 7,253,736 B2
(45) Date of Patent: Aug. 7, 2007

(54) RFID TAG FOR INSTRUMENT HANDLES

(75) Inventors: Steven M. Tethrake, North Webster, IN (US); Jeffrey H. Nycz, Collierville, TN (US); Mark Pelo, Macy, IN (US)

(73) Assignee: SDGI Holdings, Inc., Wilmington, DE (US)

( * ) Notice: Subject to any disclaimer, the term of this patent is extended or adjusted under 35 U.S.C. 154(b) by 371 days.

(21) Appl. No.: 10/926,299

(22) Filed: Aug. 26, 2004

(65) Prior Publication Data

US 2006/0043178 A1    Mar. 2, 2006

(51) Int. Cl.
*G08B 13/14* (2006.01)

(52) U.S. Cl. ............... 340/572.7; 235/492; 340/572.8; 343/872

(58) Field of Classification Search ............ 340/572.1, 340/572.7, 572.8, 5.92; 235/385, 492; 343/872–873; 252/500
See application file for complete search history.

(56) References Cited

U.S. PATENT DOCUMENTS

| | | | |
|---|---|---|---|
| 5,566,441 A | 10/1996 | Marsh et al. | |
| 6,018,299 A | 1/2000 | Eberhardt | |
| 6,107,920 A | 8/2000 | Eberhardt | |
| 6,259,369 B1 | 7/2001 | Monico | |
| 6,366,206 B1 | 4/2002 | Ishikawa et al. | |
| 6,662,430 B2 | 12/2003 | Brady et al. | |
| 6,667,092 B1 | 12/2003 | Brollier et al. | |
| 6,989,749 B2* | 1/2006 | Mohr | 340/572.1 |
| 2002/0067263 A1* | 6/2002 | Tafoya et al. | 340/572.1 |
| 2003/0102970 A1* | 6/2003 | Creel et al. | 340/572.1 |
| 2003/0235027 A1 | 12/2003 | Smeyak et al. | |
| 2004/0173781 A1* | 9/2004 | Lawrence et al. | 252/500 |
| 2005/0057424 A1* | 3/2005 | Kukko et al. | 348/873 |

(Continued)

FOREIGN PATENT DOCUMENTS

WO    WO-01/24109    4/2001

(Continued)

OTHER PUBLICATIONS

Presentation by Innovision Research and Technology, PLC at the "RFID in Healthcare" conference in Washington, DC on Dec. 2 and 3, 2003 (23 pages).

(Continued)

*Primary Examiner*—Thomas Mullen
(74) *Attorney, Agent, or Firm*—Hunton & Williams LLP

(57) ABSTRACT

Disclosed are exemplary implementations of an instrument having an RFID tag formed in or on the material of its handle. One or more antenna segments of the RFID tag may be formed from conductive material printed on or otherwise applied to a surface of the material or they may be formed from a conductive foil or other preformed material applied to the surface of the elastic material of the instrument handle. The antenna segments may be configured to represent at least a portion of a graphic, such as a company logo, for viewing by a user or handler of the instrument. At least a portion of the RFID tag and surrounding of the instrument handle may be covered by a protective material to prevent damage to the RFID tag as a result of repeated handling or subjection of the instrument to autoclaving, sterilization or caustic materials.

20 Claims, 5 Drawing Sheets

U.S. PATENT DOCUMENTS

2005/0088304 A1* 4/2005 Hines et al. .............. 340/572.1
2005/0284941 A1* 12/2005 Lubow ....................... 235/492

FOREIGN PATENT DOCUMENTS

WO    WO-2004/057528    7/2004

OTHER PUBLICATIONS

Paper, Film & Foil Converter (PFFC) RFID and Conductive Inks: What You Need to Know, Nsenga Byrd Thompson, Associate Editor, Online Exclusive, Jan. 15, 2004, http://pffc-online.com/microsites/newsarticle.asp?mode=print&newsarticleid=2708965&re . . . (3 pages).

Tracking RFID Progress, American Printer (A Primedia Publication), Jan. 1, 2004, http://americanprinter.com/microsites/magazinearticle.asp?mode=print&magazinearticleid . . . (3 pages).

EETimes T-INK™ Unique Conductive Ink Technology to Be Featured Feb. 14, 2003, URL:http://www.eetimes.com/showPressRelease.jhtml?articleID=57907 (2 pages).

RFID Journal, Can RFID Cure Healthcare's Ills?, http://rfidjournal.com/article/view/112 (2 pages).

USA Today, Conductive ink advances electronics, By Peter Svennson, The Associated Press, http://usatoday.printhis.clickability.com/pt/cpt?action=cpt&expire=&urlID=8067862&fb=. . . .

* cited by examiner

RFID TAG FOR INSTRUMENT HANDLES

FIELD OF THE INVENTION

The present invention relates generally to radio frequency identification (RFID) tags and more particularly to the use of RFID tags on instrument handles.

BACKGROUND OF THE INVENTION

Radio frequency identification (RFID) tags frequently are used to track items as they are manufactured, shipped, or otherwise handled. In general, conventional RFID tags are created by forming a radio frequency (RF) antenna on a firm, solid substrate, such as hard plastic, paper or cardboard. An RFID chip having circuitry to enable the RFID functions is positioned on or near the RF antenna and the contacts of the RFID chip are electrically connected to the RF antenna. The RFID tag then may be attached to the tracked product or attached to a package, bill or envelope associated with the tracked product.

While conventional RFID techniques are appropriate in many circumstances, these techniques have a number of shortcomings when used to implement RFID tags on instruments such as surgical instruments (e.g., scalpels, forceps and extractors), hand-held repair tools (e.g., screwdrivers, pliers and hammers), power tools (e.g., drills and nail guns), and the like. In many instances, much of an instrument may not be suitable for application of an RFID tag. To illustrate, many surgical instruments are substantially formed from conductive material, such as stainless steel, so the RFID tag typically needs a dielectric substrate to insulate the antenna from the conductive material of the instrument. However, many conventional dielectric substrates are impracticable in view of the uses and handling of the instrument. For example, the use of a paper or cardboard substrate generally is impracticable on surgical instruments due to the autoclaving and sterilization processes they often undergo. Similarly, paper- or cardboard-backed RFID tags frequently deteriorate to the point of being useless after frequent handling of an instrument. Those conventional RFID tag substrates that have some ability to withstand the rigors of frequent use or autoclaving/sterilization processes typically lack the ability to conform adequately to the contours of the instrument and thus can only be implemented on certain areas of the instrument which may be inconvenient or impracticable in use or when scanning the instrument using an RFID scanner.

The description herein of problems and disadvantages of known apparatus, methods, and devices is not intended to limit the invention to the exclusion of these known entities. Indeed, embodiments of the invention may include one or more of the known apparatus, methods, and devices without suffering from the disadvantages and problems noted herein.

SUMMARY OF THE INVENTION

An improved RFID tag for use on an instrument and a method for its implementation would be advantageous.

Embodiments of the present invention mitigate or solve the above-identified limitations in known solutions, as well as other unspecified deficiencies in known solutions. A number of advantages associated with the present invention are readily evident to those skilled in the art, including economy of design and resources, transparent operation, cost savings, etc.

In accordance with one embodiment of the present invention, an instrument is provided. The instrument comprises a handle having a non-metallic material positioned on at least a portion of the handle, the non-metallic portion having at least one surface and a radio frequency identification (RFID) chip positioned at a surface of the non-metallic material of the handle. The instrument also comprises one or more radio frequency (RF) antenna segments positioned at a surface of the non-metallic material of the handle and operably connected to the RFID chip. The RFID chip may positioned at least partially in a depression formed in the non-metallic material of the handle. Alternatively, the RFID chip may be positioned on top of the surface of the non-metallic material of the handle.

The instrument may further comprise a protective layer positioned over at least a portion of at least one of the one or more RF antenna segments. The protective layer may be further positioned over at least a portion of the RFID chip and at least a portion of the surface of the non-metallic material of the handle. The protective layer may comprise a substantially transparent material.

In accordance with another embodiment of the present invention, a method for implementing a radio frequency identification (RFID) tag in an instrument handle having a non-metallic material containing at least one surface and positioned on at least a portion of the instrument handle is provided. The method comprises positioning an RFID chip at a surface of the non-metallic material of the instrument handle and depositing conductive material on a surface of the non-metallic material of the instrument handle to form one or more radio frequency (RF) antenna segments. The method may further comprise forming a depression in a surface of the non-metallic material of the instrument handle, where positioning the RFID chip comprises positioning the RFID chip at least partially in the depression. Alternatively, positioning the RFID chip may comprise positioning the RFID on top of a surface of the non-metallic material of the handle.

The method may further comprise depositing a protective layer over at least a portion of at least one of the one or more RF antenna segments. The protective layer may be further positioned over at least a portion of the RFID chip and at least a portion of the surface of the non-metallic material of the handle. The protective layer may comprise a substantially transparent material.

At least one of the one or more RF antenna segments comprises conductive foil positioned on a surface of the non-metallic material of the handle. Alternatively, at least one of the one or more RF antenna segments comprises conductive ink positioned on the surface of the elastic material of the handle. One or more RF antenna segments may be arranged to represent at least a portion of a graphic. The graphic may include at least one selected from the group consisting of a company logo, a warning label, text, and combinations thereof.

The instrument may comprise a surgical instrument. The RF antenna segments therefore may comprise one or more materials that are substantially unaffected by an autoclaving process or a sterilization process.

The non-metallic material may comprise an elastic material. Examples of the elastic material include, but are not limited to, silicone, latex, natural rubber, synthetic rubber, and elastic polymers.

Still further features and advantages of the present invention are identified in the ensuing description, with reference to the drawings identified below.

BRIEF DESCRIPTION OF THE DRAWINGS

The purpose and advantages of the present invention will be apparent to those of ordinary skill in the art from the following detailed description in conjunction with the appended drawings in which like reference characters are used to indicate like elements, and in which.

DETAILED DESCRIPTION OF THE INVENTION

The following description is intended to convey a thorough understanding of the present invention by providing a number of specific embodiments and details involving implementing RFID tags in surgical instruments, and in particular to soft-handled instruments. It is understood, however, that the present invention is not limited to these specific embodiments and details, which are exemplary only. It is further understood that one possessing ordinary skill in the art, in light of known systems and methods, would appreciate the use of the invention for its intended purposes and benefits in any number of alternative embodiments, depending upon specific design and other needs.

FIGS. 1-6 illustrate exemplary implementations of instruments having RFID tags formed in or on the material of the instrument handles having at least a portion of its surface comprised of, or covered by, a non-metallic material such as a hard plastic or polymeric material, or alternatively, an elastic, or "soft," material. Throughout this description, the expression "non-metallic material" denotes materials that include at least a portion of a non-metallic element, even though other portions of the handle may be metallic. Examples of suitable materials for forming the handle of an instrument include, but are not limited to, polyethylene, polypropylene, polybutylene, polybutadiene, styrene, polystyrene, copolymers of these materials such as polybutadiene/polystyrene, polyethylene/propylene, and terpolymers or higher mers of the respective monomers, natural rubber (e.g., gum rubber), synthetic rubbers (e.g., neoprene polychloroprene), amorphous thermoplastics (e.g., polyphenylsulfone, also known as Radel R) and other elastic polymers and elastomers, latex, silicone, and the like. The RF antenna segments of the RFID tag may be formed at least in part from conductive ink printed on or otherwise applied to a surface of the material of the instrument handle or they may be formed from a conductive foil applied to the surface of the material of the instrument handle. In at least one embodiment, the antenna segments are arranged to represent at least part of a graphic, such as a company logo, for viewing by a user or handler of the instrument.

Non-metallic-handled instruments with which RFID tags may be advantageously implemented may include, but are not limited to, medical instruments such as scalpels, forceps, clamps, etc., hand-held construction and repair tools such as screwdrivers, hammers, wrenches, pliers, etc., powered tools such as drills, circular saws, nail guns, etc., as well as other various tools, instruments or other implements where the benefits of a more-secure grip, vibration dampening, or improved ergonomics provided by the non-metallic material handles are useful or desired.

Figure 1:
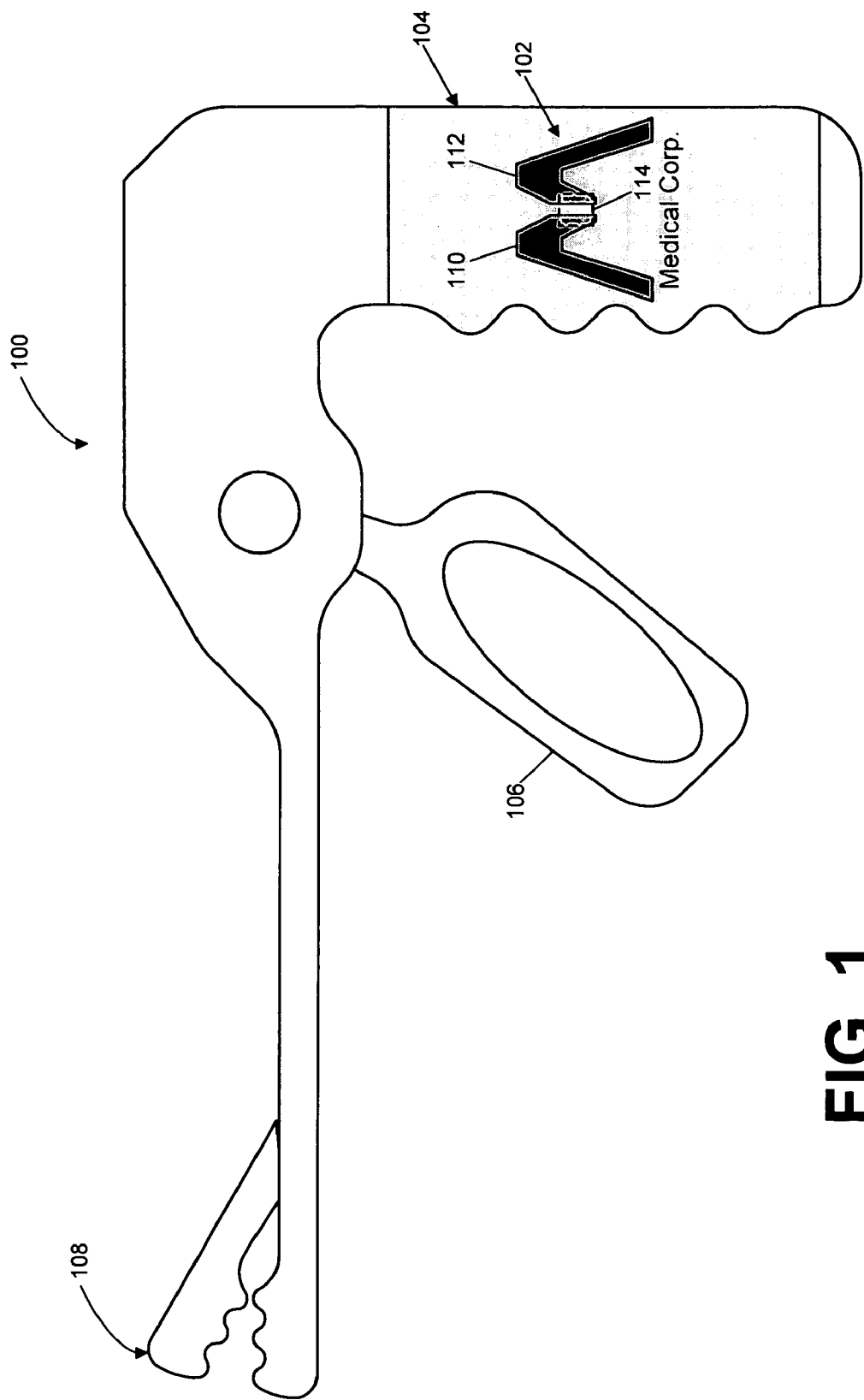
FIG. 1 is a side view of an exemplary instrument having an RFID tag positioned on the material of its handle in accordance with at least one embodiment of the present invention.
Figure 2:
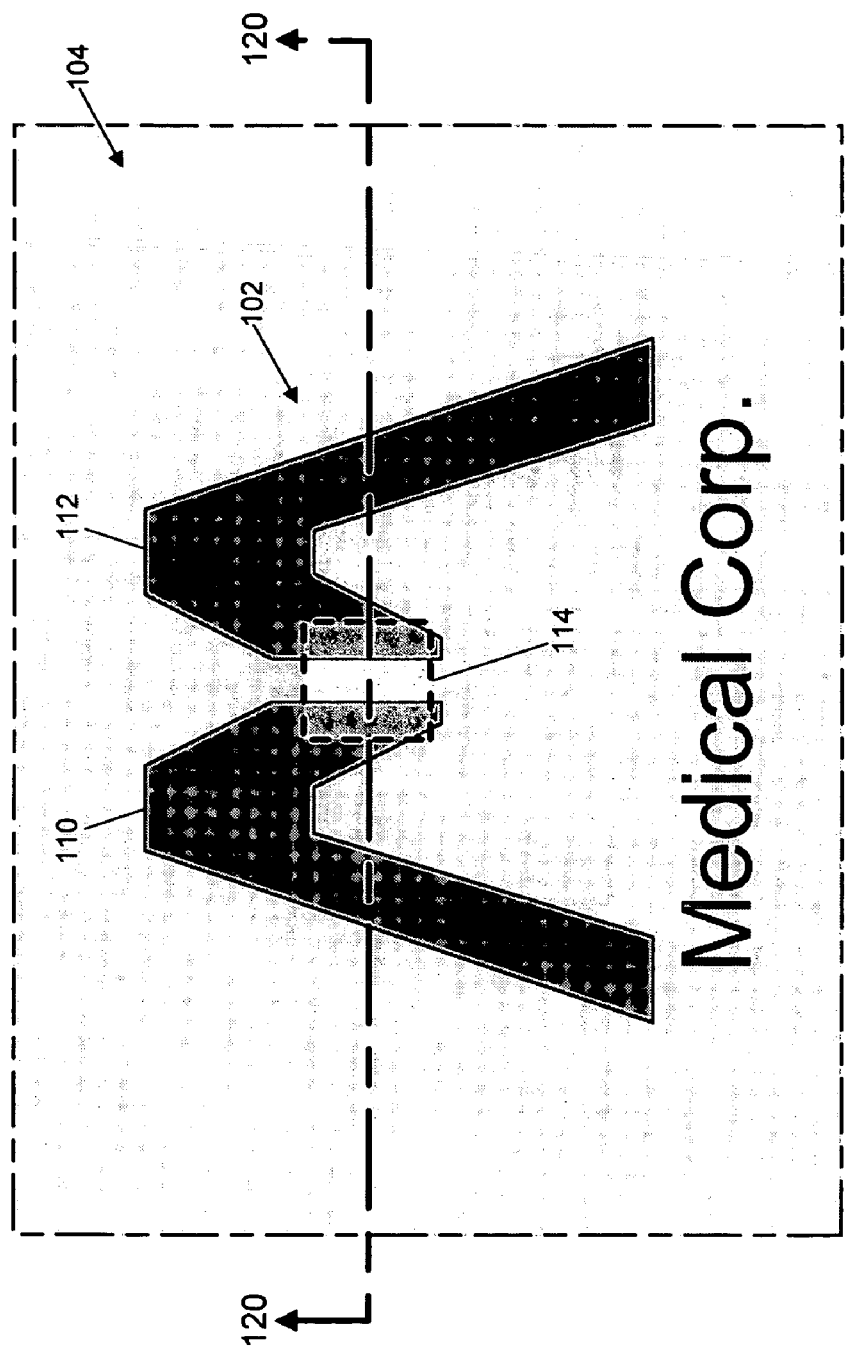
FIG. 2 is an enlarged view of the exemplary RFID tag of FIG. 1 in accordance with at least one embodiment of the present invention.

Referring now to FIGS. 1 and 2, an exemplary instrument 100 having an RFID tag 102 attached thereto is illustrated in accordance with at least one embodiment of the present invention. In the illustrated example, the instrument 100 includes a handle 104 to allow a user to manipulate the instrument 100 and/or operate one or more features of the instrument 100 (e.g., manipulating the handle 104 and lever 106 to open and close jaws 108). The handle 104 may include a rigid core or skeleton formed from a rigid material, such as, for example, steel, aluminum, hard plastic or other hard polymers, carbon fiber, and the like, and further includes one or more non-metallic materials that cover at least a portion of the core or skeleton of the handle 104 to secure or comfort the grip of a user. Alternatively, the handle 104 may be formed substantially from one or more non-metallic materials.

In the illustrated example, one or more RFID tags 102 are disposed in or on the material of the handle 104 of the instrument 100. Various considerations may be taken into account in determining a suitable location on the handle 104 for the RFID tag 102. For example, it may be desirable to locate the RFID tag 102 in a location on the elastic material of the handle 104 that is likely to be touched less frequently by a user (such as, for example, on the bottom of the handle 104). Alternatively, it may be desirable to dispose the RFID tag 102 on the material of the handle 104 in a location that allows for suitable access by an RFID tag reader (not shown). As discussed in greater detail below, in at least one embodiment, the one or more antenna segments 110, 112 of the RFID tag 104 may comprise a logo or other graphic formed from conductive ink disposed on the material of the handle 104. In such an instance, it may be desirable to locate the RFID tag 102 such that at least the antenna segments 110, 112 are readily visible to an observer.

As illustrated in FIG. 2, the RFID tag 102 preferably includes an RFID chip 114 electrically connected to one or more RF antennas (as represented by RF antenna segments 110, 112). The RFID tag 102 may comprise a passive RFID tag, wherein operating power for the RFID chip 114 is obtained from an RF signal output by an RFID reader. Alternatively, the RFID tag 102 may comprise a semi-passive or active RFID tag wherein operating power is supplied by a battery or other power source collocated with the RFID tag. In either instance, the RFID tag 102 may be read only or readable/writable. If the RFID tag 102 is implemented as a semi-passive or active RFID chip, the RFID tag 102 may further include a power source (not shown), such as a small battery, solar panel, etc. that is operably connected to the RFID chip 114 and may be embedded in or on the material of the handle 104 or at another suitable location.

The RFID chip 114 also may include one or more contacts 310, 312 (e.g., pins or pads—see, FIG. 3) for electrical connection to one or more antenna segments 110, 112. Although the RF antenna of the RFID tag 102 is exemplarily illustrated as having two antenna segments 110, 112 for ease of illustration, any number of antenna segments or any antenna configuration may be implemented as appropriate under the conditions without departing from the spirit or the scope of various embodiments of the present invention.

In one embodiment, the RFID chip 114 of the RFID tag 102 is disposed below the antenna segments 110, 112 by, for example, positioning the RFID chip 114 in a depression formed in the material of the handle 104 (as illustrated in greater detail with reference to FIGS. 3 and 4). In another embodiment, the RFID chip 114 is positioned above the antenna segments 110, 112 by, for example, positioning the RFID chip 114 on the material of the handle 104 after forming the antenna segments 110, 112 on or in the handle 104 (as illustrated in greater detail with reference to FIGS. 5 and 6).

The antenna segments 110, 112 may be formed on or in the handle 104 using any of a variety of techniques. For example, in one embodiment, trenches or other depressions in the desired shape of the antenna segments 110, 112 may be formed in the handle 104 and a conductive material, such as, for example, silver paste, may be deposited into the trenches to form the antenna segments 110, 112. In another embodiment, the antenna segments 110, 112 may be preformed from a conductive material (e.g., copper or aluminum foil) and then positioned on the surface of the handle 104. In such instances, the preformed conductive material comprising the antenna segments 110, 112 may be attached to the handle 104 using glue or by coating the preformed antenna segments 110, 112 and the surrounding surface of the handle 104 with a material such that the preformed antenna segments 110, 112 are lacquered to the surface of the handle 104.

Alternatively, in at least one embodiment, the antenna segments 110, 112 may be formed at least in part from conductive ink applied to the surface of the handle 104 using one or more conductive ink printing techniques. Examples of suitable printing techniques include analogue printing or digital printing techniques, such as: screen printing; piezo impulse drop on demand; piezo shared wall impulse drop on demand; thermal inkjet drop on demand; binary continuous inkjet; multi-deflection continuous inkjet; and the like. Other printing techniques or conductive ink application techniques may be implemented without departing from the spirit or the scope of certain embodiments of the present invention.

As noted above, the conductive ink of the antenna segments 110, 112 may be applied to form part or all of a graphic on the surface of the elastic material of the handle 104. This graphic may represent a logo of an entity, such as, for example, a manufacturer, supplier, distributor, or user of the instrument 100. Alternatively, the graphic may represent a warning label or other visual indicator, such as, for example, a biohazard warning. The graphic also may include text providing, for example, instructions for use of the instrument 100, identification information for the instrument 100, and the like. It will be appreciated that various characteristics of the antenna segments 110, 112, such as the dimension, shape and type of the conductive ink forming the antenna segments 110, 112, may be affected by one or more operational characteristics of the RFID tag 102, such as operating frequency, desired read range, material used, and the like. Accordingly, to take these operational characteristics into account the shape, dimension, or proportions of the graphic may be altered, non-conductive material may be substituted in certain areas of the graphic, the contacts between the RFID chip 114 and the antenna segments 110, 112 may be selected, and the like.

As noted above, conductive ink may be applied on or in the non-metallic material of the handle 104 to form at least part of the antenna segments 110, 112. Thus, a conductive ink suitable to the elastic conditions of the handle 104 preferably is selected. Examples of suitable conductive inks include high-viscosity silver liquid, silver liquid paste, silver chloride paste, graphite/carbon paste, conductive polymers, and the like. Commercial examples of suitable conductive inks include PTF-10, PTF-10A, PTF 20, PTF-22, PTF-30, and PTF-61, all available from Advanced Conductive Materials, Inc. of Atascadero, Calif.

Additionally, the instrument 100 may comprise a medical instrument or other type of instrument subjected to autoclaving or sterilization, immersion in caustic fluids, or other deleterious actions. The type of conductive ink therefore may be selected based in part on its resistance to high temperatures, steam or caustic materials. Moreover, as the RFID tag 102 may be placed on or near the surface of the handle 104, it is possible that the conductive ink forming at least part of the antenna segments 110, 112 may be subjected to frequent wear as it is touched by a user of the instrument 100. Accordingly, the conductive ink may be selected for its resistance to wear or, as discussed in detail below, additional protective material may be applied over the conductive ink to prevent erosion of the conductive ink during use of the instrument 100.

Figure 3:
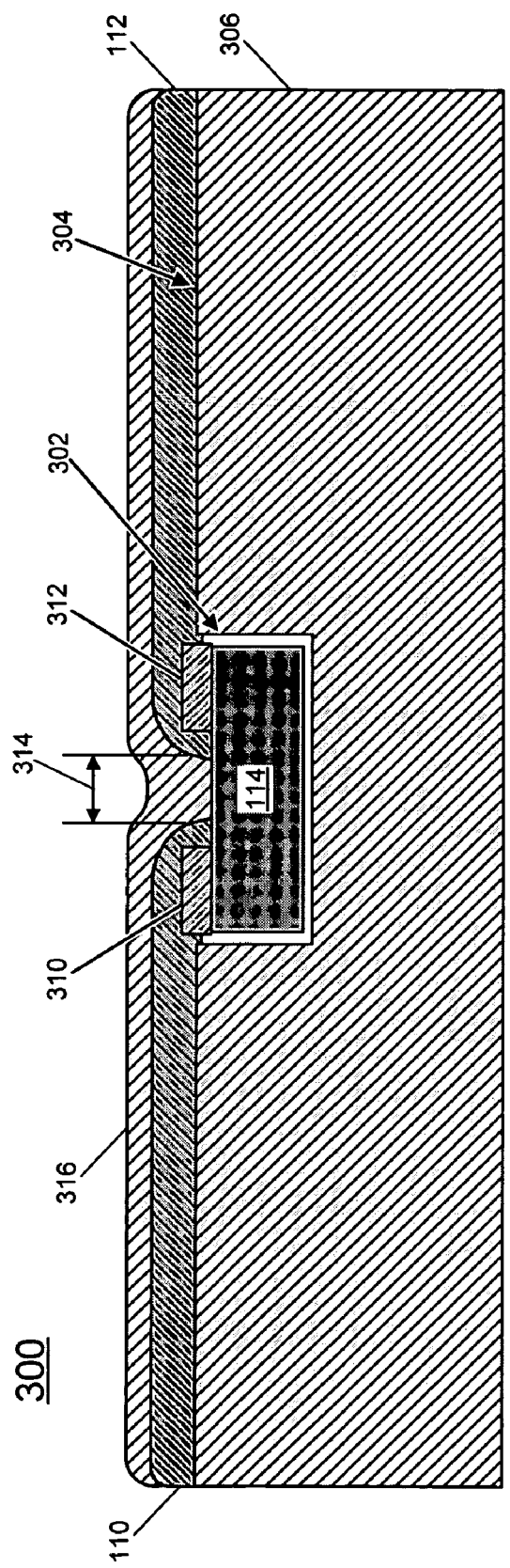
FIGS. 3 and 5 are exemplary cross-section views of the RFID tag of FIG. 2 in accordance with at least one embodiment of the present invention.
Figure 4:
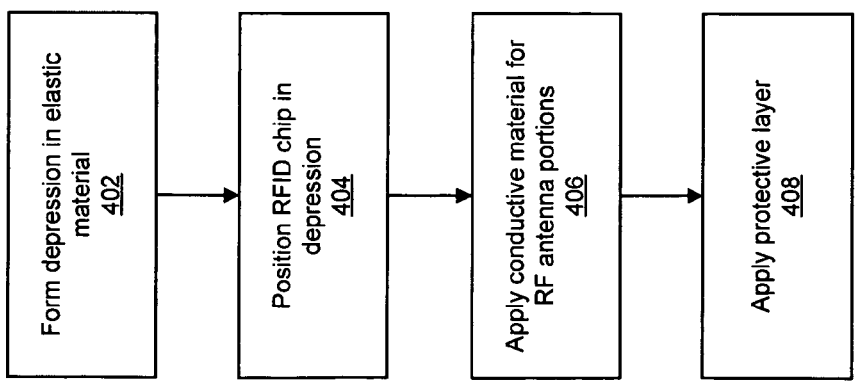

Referring now to FIGS. 3 and 4, an exemplary cross-section view 300 (FIG. 3) of the RFID tag 102 and handle 104 of the instrument 100 along line 120 of FIG. 2 and a corresponding exemplary method 400 (FIG. 4) for forming the RFID tag 102 for instrument 100 are illustrated in accordance with at least one embodiment of the present invention. In the illustrated embodiment, the exemplary method 400 initiates at step 402 by forming a depression 302 at the surface 304 of the non-metallic material 306 of the handle 104. The depression 302 may be formed in the non-metallic material 306 during the molding process, by removing material after the molding process, or by depressing the surface 304 so that the depression 302 is created. At step 404, an RFID chip 114 is positioned at least partially in the depression 302, where the RFID chip 114 preferably is oriented so that one or more of the electrical contacts 310, 312 intended for connection to the antenna segments 110, 112 are accessible from the surface 304. The depression 302 may be formed to have substantially the same dimensions as the body of the RFID chip 114 so as to hold the RFID chip 114 in place by friction, or adhesives or other materials may be used to maintain the position of the RFID chip 114 in the depression 302.

At step 406, the antenna segments 110, 112 may be positioned on the surface 304. As described above, the antenna segments 110, 112 may comprise conductive foil applied to the surface 304 or may comprise conductive ink printed on or otherwise applied to the surface 304. As illustrated in FIG. 3, the antenna segments 110, 112 preferably are applied/printed such that they come into electrical contact with the corresponding contacts 310, 312 of the RFID chip 114 while a gap 314 remains between the antenna segments 110, 112 so as to prevent shorting of the resulting RF antenna. Alternatively, conductive foil or wire may be used to electrically connect the antenna segments 110, 112 to the corresponding contacts 310, 312.

As noted above, the instrument 100 may comprise a surgical instrument or other tool subject to autoclaving, sterilization, or repeated handling. To protect the integrity of the antenna segments 110, 112, a conductive ink or other conductive material suitable for such conditions may be selected for use in forming the antenna segments 110, 112. In addition, or alternatively, a protective layer 316 may be positioned over some or all of the antenna segments 110, 112, the RFID chip 114 and/or the surrounding areas of the surface 304 at step 408. In the illustrated example, the protective layer 316 is positioned over both antenna segments 110, 112 and the gap 314. In other embodiments, the protective layer may be positioned over some or all of each antenna segment separately.

In one embodiment, the protective layer 316 includes a rigid or elastic dielectric material, such as, for example, silicone, rubber, latex, lacquer, thermoplastic, epoxy, and the like, which may protect the RFID tag 102 from excessive wear, extreme temperatures and/or caustic chemicals. In instances wherein the antenna segments 110, 112 form part or all of a graphic, the protective layer 316 preferably comprises a substantially transparent material when cured or dried to allow viewing of the graphic represented by the antenna segments 110, 112. In other embodiments, the protective layer 316 may include a conductive material disposed over one or both antenna segments. To illustrate, the antenna segments 110, 112 may be formed from a thicker layer of silver paste conductive ink, for example, whereas the protective layer 316 may be formed from a thinner layer of dyed conductive ink to provide the desired color. In this instance, an additional, non-conductive protective layer may be formed over the conductive protective layer.

Figure 6:
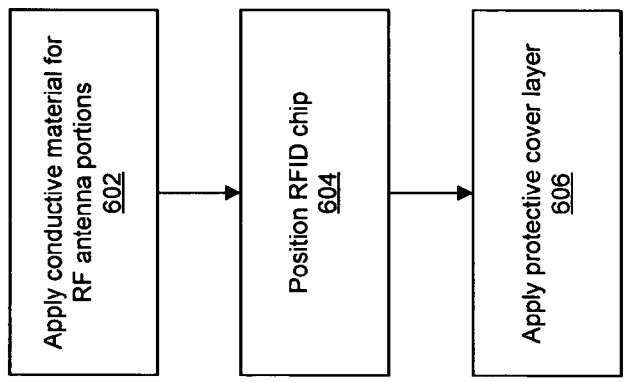
FIGS. 4 and 6 are exemplary methods for forming the RFID tag of FIG. 2 in accordance with at least one embodiment of the present invention.
Figure 5:
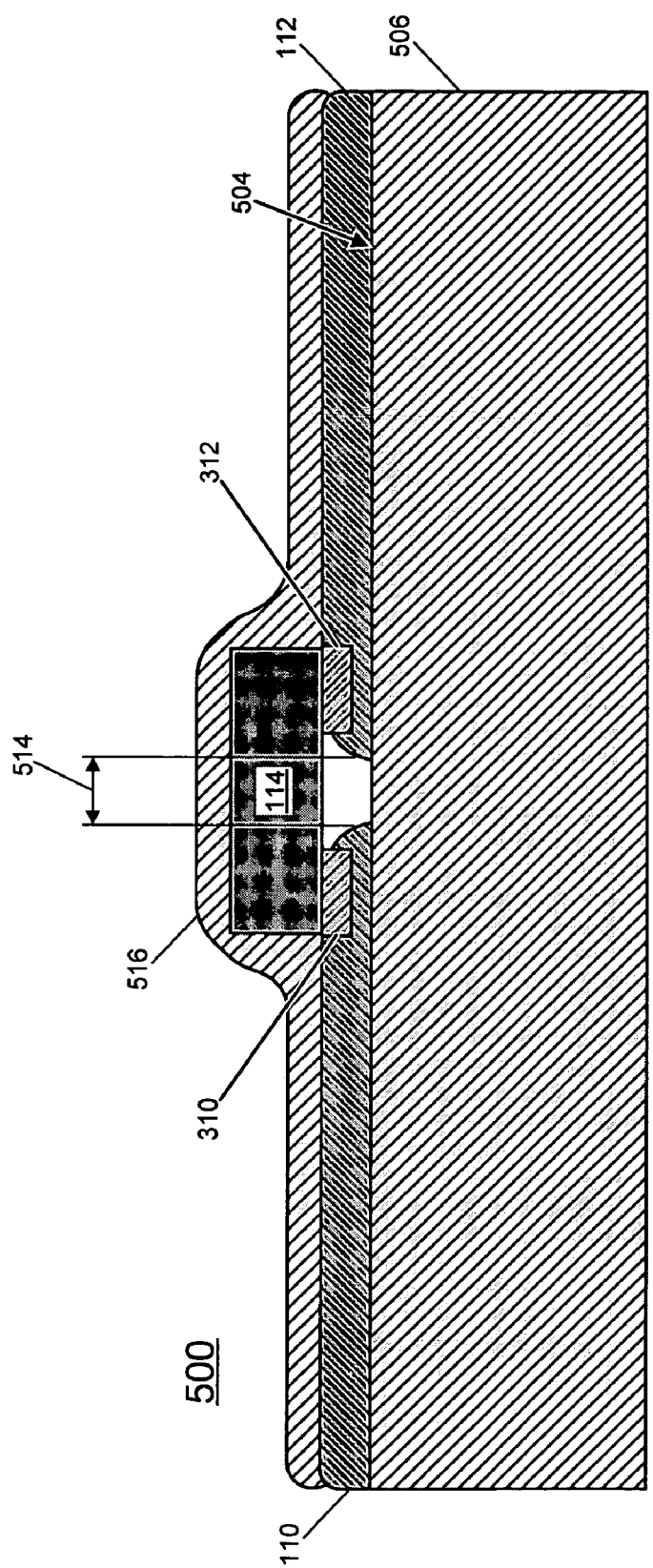

Referring now to FIGS. 5 and 6, another exemplary cross-section view 500 (FIG. 5) of the RFID tag 102 and handle 104 of the instrument 100 along line 120 of FIG. 2 and a corresponding exemplary method 600 (FIG. 6) for forming the RFID tag 102 for instrument 100 are illustrated in accordance with at least one embodiment of the present invention. In the illustrated embodiment, the exemplary method 600 initiates at step 602 by positioning the antenna segments 110, 112 on or in a surface 504 of the non-metallic material 506 of the handle 104. The antenna segments 110, 112 may comprise conductive foil applied to or formed in the surface 504 or may comprise conductive ink printed on or otherwise applied to the surface 504.

At step 604, an RFID chip 114 is positioned on the surface 504 and may be secured to the surface 504 using an adhesive or other material. In the illustrated embodiment, the RFID chip 114 is positioned at a gap 514 between the antenna segments 110, 112 such that each of the contacts 310, 312 are placed in direct electrical contact with a corresponding one of the antenna segments 110, 112. In instances where the antenna segments 110, 112 are comprised of conductive ink that cures or dries, the RFID chip 114 may be positioned on the surface 504 after the application of the conductive ink but before the conductive ink has cured or dried so that the contacts 310, 312 may be secured to the antenna segments 110, 112 as a result of the curing/drying process. In other embodiments, the contacts 310, 312 may be connected to the corresponding antenna segments 110, 112 using conductive foil, wires, and the like.

To protect the integrity of the antenna segments 110, 112 or to secure the RFID chip 114 on the surface 504, a protective layer 516 may be positioned over some or all of the antenna segments 110, 112, the RFID chip 114 and/or the surrounding areas of the surface 504 at step 606. The protective layer 516 may include a flexible or rigid dielectric material to protect the RFID tag 102 from excessive wear, extreme temperatures and/or caustic chemicals and preferably comprises a material that is substantially transparent when dried or cured to allow viewing of a graphic represented by the antenna segments 110, 112. In other embodiments, the protective layer 516 may include a conductive material positioned over one or both antenna segments, and an additional non-conductive protective layer may be formed over the conductive protective layer 516.

Other embodiments, uses, and advantages of the invention will be apparent to those skilled in the art from consideration of the specification and practice of the invention disclosed herein. The specification and drawings should be considered exemplary only, and the scope of the invention is accordingly intended to be limited only by the following claims and equivalents thereof.

What is claimed is:

1. An instrument comprising:
   a handle having a non-metallic material positioned on at least a portion of the handle, the non-metallic material having at least one surface;
   a radio frequency identification (RFID) chip positioned at a surface of the non-metallic material of the handle; and
   one or more radio frequency (RF) antenna segments positioned at a surface of the non-metallic material of the handle and operably connected to the RFID chip, wherein the one or more antenna segments are formed on the surface in a graphic image pattern, the graphic image pattern comprising at least one graphic image selected from the group consisting of a company logo, a warning label, text, and combinations thereof, and further comprising a substantially transparent protective layer positioned over at least a portion of the one or more antenna segments.

2. The instrument as in claim 1, wherein the transparent protective layer is further positioned over at least a portion of the RFID chip and at least a portion of the surface of the non-metallic material of the handle.

3. The instrument as in claim 1, wherein at least one of the one or more RF antenna segments comprises conductive foil positioned on a surface of the non-metallic material of the handle.

4. The instrument as in claim 1, wherein at least one of the one or more RF antenna segments comprise conductive ink deposited on the surface of the elastic material of the handle.

5. The instrument as in claim 1, wherein the instrument is a surgical instrument.

6. The instrument as in claim 5, wherein the RF antenna segments comprise one or more materials that are substantially unaffected by an autoclaving process or a sterilization process.

7. The instrument as in claim 1, wherein the RFID chip is positioned at least partially in a depression formed in the non-metallic material of the handle.

8. The instrument as in claim 1, wherein the RFID chip is positioned on top of the surface of the non-metallic material of the handle.

9. The instrument as in claim 1, wherein the non-metallic material comprises an elastic material.

10. The instrument as in claim 9, wherein the elastic material includes at least one selected from the group consisting of: silicone; latex; natural rubber; synthetic rubber; and elastic polymers.

11. A method for implementing a radio frequency identification (RFID) tag in an instrument handle having a non-metallic material containing at least one surface that is positioned on at least a portion of the instrument handle, the method comprising:
    positioning an RFID chip at a surface of the non-metallic material of the instrument handle; and
    depositing conductive material on a surface of the non-metallic material of the instrument handle to form one or more radio frequency (RF) antenna segments, wherein the conductive material is deposited in a pattern so as to form at least one graphic image selected from the group consisting of a company logo, a warning label, text, and combinations thereof; and
    depositing a substantially transparent protective layer over at least a portion of the one or more RF antenna segments.

12. The method as in claim 11, wherein the protective layer is further positioned over at least a portion of the RFID chip and at least a portion of the surface of the non-metallic material of the handle.

13. The method as in claim 11, wherein the conductive material comprises conductive foil.

14. The method as in claim 11, wherein the conductive material comprises conductive ink.

15. The method as in claim 11, wherein the instrument is a surgical instrument.

16. The method as in claim 15, wherein the conductive material comprises one or more materials that are substantially unaffected by an autoclaving process or a sterilization process.

17. The method as in claim 11, further comprising forming a depression in a surface of the non-metallic material of the instrument handle, and wherein positioning the RFID chip comprises positioning the RFID chip at least partially in the depression.

18. The method as in claim 11, wherein positioning the RFID chip comprises positioning the RFID chip on top of a surface of the non-metallic material of the handle.

19. The method as in claim 11, wherein the non-metallic material comprises an elastic material.

20. The method as in claim 19, wherein the elastic material includes at least one selected from the group consisting of: silicone; latex; natural rubber; synthetic rubber; and elastic polymers.

* * * * *